United States Patent
O'Prey et al.

(10) Patent No.: US 8,579,810 B2
(45) Date of Patent: Nov. 12, 2013

(54) EXPANDABLE THORACIC ACCESS PORT

(75) Inventors: Cormac O'Prey, Bishops Stortford (GB); Jennifer Rachel Gell, Cambridge (GB); Charlotte Adele Clark, Cambridge (GB); Fiona Middlemiss Haig, Histon (GB)

(73) Assignee: Covidien LP, Mansfield, MA (US)

( * ) Notice: Subject to any disclaimer, the term of this patent is extended or adjusted under 35 U.S.C. 154(b) by 170 days.

(21) Appl. No.: 13/005,616

(22) Filed: Jan. 13, 2011

(65) Prior Publication Data

US 2011/0201894 A1    Aug. 18, 2011

Related U.S. Application Data

(60) Provisional application No. 61/304,111, filed on Feb. 12, 2010.

(51) Int. Cl.
*A61B 1/32* (2006.01)

(52) U.S. Cl.
USPC .......................................................... 600/219

(58) Field of Classification Search
USPC ......... 600/201–204, 210, 214–216, 219, 222, 600/231, 233
See application file for complete search history.

(56) References Cited

U.S. PATENT DOCUMENTS

| | | | |
|---|---|---|---|
| 1,780,912 A | 11/1930 | Gau | |
| 1,810,466 A | 6/1931 | Deutsch | |
| 2,313,164 A | 3/1943 | Nelson | |
| 2,541,516 A | 2/1951 | Ivory et al. | |
| 2,812,758 A | 11/1957 | Blumenschein | |
| 3,774,596 A * | 11/1973 | Cook | 600/184 |
| 3,782,370 A * | 1/1974 | McDonald | 600/207 |
| 3,807,393 A | 4/1974 | McDonald | |
| 3,965,890 A | 6/1976 | Gauthier | |
| 4,130,113 A | 12/1978 | Graham | |
| 4,141,364 A * | 2/1979 | Schultze | 128/207.15 |
| 4,263,899 A | 4/1981 | Burgin | |
| 4,553,537 A | 11/1985 | Rosenberg | |
| 5,007,900 A | 4/1991 | Picha et al. | |

(Continued)

FOREIGN PATENT DOCUMENTS

DE    10001695         2/2001
DE    10001695 A1      2/2001

(Continued)

OTHER PUBLICATIONS

European Search Report EP 11 25 0719 dated Nov. 16, 2011.

(Continued)

*Primary Examiner* — Nicholas Woodall

(57) ABSTRACT

A surgical access assembly includes first and second wings disposed in opposed relation relative to one another. Each wing includes a body portion, a distal portion and first and second portions. A side wall section hingedly connects the body portions of the wings to one another at the first portion thereof and at the second portions thereof. Each of the side wall sections is movable with respect to the other side wall sections between a first position and a second position wherein each of the side wall sections is angled with the first and second wings. The first and second wings are moveable between an approximated position corresponding to the first position of the side wall sections and a spaced apart position corresponding to the second position of the side wall sections.

16 Claims, 4 Drawing Sheets

(56) References Cited

U.S. PATENT DOCUMENTS

| | | | |
|---|---|---|---|
| 5,052,374 A | 10/1991 | Alvarez-Jacinto |
| 5,080,088 A | 1/1992 | LeVahn |
| 5,125,396 A | 6/1992 | Ray |
| 5,169,387 A | 12/1992 | Kronner |
| 5,231,974 A | 8/1993 | Giglio et al. |
| 5,232,451 A | 8/1993 | Freitas et al. |
| 5,269,754 A | 12/1993 | Rydell |
| 5,279,575 A | 1/1994 | Sugarbaker |
| 5,330,501 A | 7/1994 | Tovey et al. |
| 5,346,484 A | 9/1994 | Van Lindert |
| 5,391,156 A | 2/1995 | Hildwein et al. |
| 5,437,683 A | 8/1995 | Neumann et al. |
| 5,445,615 A | 8/1995 | Yoon |
| 5,460,170 A | 10/1995 | Hammerslag |
| 5,480,410 A | 1/1996 | Cuschieri |
| 5,490,843 A | 2/1996 | Hildwein et al. |
| 5,503,617 A | 4/1996 | Jako |
| 5,520,610 A | 5/1996 | Giglio et al. |
| 5,524,644 A | 6/1996 | Crook |
| 5,556,385 A | 9/1996 | Andersen |
| 5,562,677 A | 10/1996 | Hildwein et al. |
| 5,653,705 A | 8/1997 | De la Torre et al. |
| 5,697,891 A | 12/1997 | Hori |
| 5,728,103 A | 3/1998 | Picha et al. |
| 5,755,660 A | 5/1998 | Tyagi |
| 5,755,661 A | 5/1998 | Schwartzman |
| 5,772,583 A | 6/1998 | Wright et al. |
| 5,776,110 A | 7/1998 | Guy et al. |
| 5,779,629 A | 7/1998 | Hohlen |
| 5,788,630 A | 8/1998 | Furnish |
| 5,803,921 A | 9/1998 | Bonadio |
| 5,810,721 A | 9/1998 | Mueller et al. |
| 5,846,193 A | 12/1998 | Wright |
| 5,875,782 A | 3/1999 | Ferrari et al. |
| 5,879,291 A | 3/1999 | Kolata et al. |
| 5,906,577 A | 5/1999 | Beane et al. |
| 5,908,382 A | 6/1999 | Koros et al. |
| 5,931,778 A | 8/1999 | Furnish |
| 5,935,107 A | 8/1999 | Taylor et al. |
| 5,944,736 A | 8/1999 | Taylor et al. |
| 5,951,466 A | 9/1999 | Segermark et al. |
| 5,951,467 A | 9/1999 | Picha et al. |
| 5,957,835 A | 9/1999 | Anderson et al. |
| 5,967,972 A | 10/1999 | Santilli et al. |
| 5,993,385 A | 11/1999 | Johnston et al. |
| 6,024,736 A | 2/2000 | De la Torre et al. |
| 6,033,362 A | 3/2000 | Cohn |
| 6,033,425 A | 3/2000 | Looney et al. |
| 6,036,641 A | 3/2000 | Taylor et al. |
| 6,074,380 A | 6/2000 | Byrne et al. |
| 6,113,535 A | 9/2000 | Fox et al. |
| 6,120,436 A | 9/2000 | Anderson et al. |
| 6,132,370 A | 10/2000 | Furnish et al. |
| 6,142,935 A | 11/2000 | Flom et al. |
| 6,159,231 A | 12/2000 | Looney et al. |
| 6,162,172 A | 12/2000 | Cosgrove et al. |
| 6,231,506 B1 | 5/2001 | Hu et al. |
| 6,254,533 B1 | 7/2001 | Fadem et al. |
| 6,254,534 B1 | 7/2001 | Butler et al. |
| 6,283,912 B1 | 9/2001 | Hu et al. |
| 6,309,349 B1 | 10/2001 | Bertolero et al. |
| 6,312,377 B1 | 11/2001 | Segermark et al. |
| 6,331,158 B1 | 12/2001 | Hu et al. |
| 6,354,995 B1 | 3/2002 | Hoftman et al. |
| 6,361,492 B1 | 3/2002 | Santilli |
| 6,382,211 B1 | 5/2002 | Crook |
| 6,443,957 B1 | 9/2002 | Addis |
| 6,450,983 B1 | 9/2002 | Rambo |
| 6,458,079 B1 | 10/2002 | Cohn et al. |
| 6,500,116 B1 | 12/2002 | Knapp |
| 6,517,563 B1 | 2/2003 | Paolitto et al. |
| 6,547,725 B1 | 4/2003 | Paolitto et al. |
| 6,585,442 B2 | 7/2003 | Brei et al. |
| 6,599,240 B2 | 7/2003 | Puchovsky et al. |
| 6,599,292 B1 | 7/2003 | Ray |
| 6,616,605 B2 | 9/2003 | Wright et al. |
| 6,652,454 B2 | 11/2003 | Hu et al. |
| 6,723,044 B2 | 4/2004 | Pulford et al. |
| 6,730,021 B2 | 5/2004 | Vassiliades, Jr. et al. |
| 6,730,022 B2 | 5/2004 | Martin et al. |
| 6,746,396 B1 | 6/2004 | Segermark et al. |
| 6,746,467 B1 | 6/2004 | Taylor et al. |
| 6,814,078 B2 | 11/2004 | Crook |
| 6,814,700 B1 | 11/2004 | Mueller et al. |
| 6,840,951 B2 | 1/2005 | De la Torre et al. |
| 6,846,287 B2 | 1/2005 | Bonadio et al. |
| 6,958,037 B2 | 10/2005 | Ewers et al. |
| 7,033,319 B2 | 4/2006 | Pulford et al. |
| 7,052,454 B2 | 5/2006 | Taylor |
| 7,144,368 B2 | 12/2006 | Larson et al. |
| 7,147,599 B2 | 12/2006 | Phillips et al. |
| 7,179,225 B2 | 2/2007 | Shluzas et al. |
| 7,195,592 B2 | 3/2007 | Ravikumar et al. |
| 7,220,228 B2 | 5/2007 | Hu et al. |
| 7,226,451 B2 | 6/2007 | Shluzas et al. |
| 7,229,408 B2 | 6/2007 | Douglas et al. |
| 7,238,154 B2 | 7/2007 | Ewers et al. |
| 7,261,688 B2 | 8/2007 | Smith et al. |
| 7,270,632 B2 | 9/2007 | Santilli |
| 7,300,399 B2 | 11/2007 | Bonadio et al. |
| 7,344,495 B2 | 3/2008 | Ravikumar et al. |
| 7,387,126 B2 | 6/2008 | Cox et al. |
| 7,393,322 B2 | 7/2008 | Wenchell |
| 7,507,202 B2 | 3/2009 | Schoellhorn |
| 7,507,235 B2 | 3/2009 | Keogh et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,566,302 B2 | 7/2009 | Schwer |
| 7,585,277 B2 | 9/2009 | Taylor et al. |
| 7,594,888 B2 | 9/2009 | Raymond et al. |
| 7,650,887 B2 | 1/2010 | Nguyen et al. |
| 2001/0002429 A1 | 5/2001 | Hu et al. |
| 2001/0020121 A1 | 9/2001 | Hu et al. |
| 2001/0041827 A1 | 11/2001 | Spence et al. |
| 2002/0004628 A1 | 1/2002 | Hu et al. |
| 2002/0095139 A1 | 7/2002 | Keogh et al. |
| 2002/0099269 A1 | 7/2002 | Martin et al. |
| 2002/0099271 A1 | 7/2002 | Knapp |
| 2002/0137989 A1 | 9/2002 | Clem et al. |
| 2003/0191371 A1 | 10/2003 | Smith et al. |
| 2004/0054353 A1 | 3/2004 | Taylor |
| 2004/0059192 A1 | 3/2004 | Cartier et al. |
| 2004/0225195 A1 | 11/2004 | Spence et al. |
| 2005/0096508 A1 | 5/2005 | Valentini et al. |
| 2005/0171403 A1 | 8/2005 | Paolitto et al. |
| 2005/0228232 A1 | 10/2005 | Gillinov et al. |
| 2005/0267336 A1 | 12/2005 | Bertolero et al. |
| 2005/0283050 A1 | 12/2005 | Gundlapalli et al. |
| 2006/0004261 A1* | 1/2006 | Douglas ............ 600/210 |
| 2006/0089537 A1 | 4/2006 | Schoellhorn |
| 2006/0106416 A1 | 5/2006 | Raymond et al. |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0155170 A1 | 7/2006 | Hanson et al. |
| 2007/0027364 A1 | 2/2007 | Schwer |
| 2007/0073110 A1 | 3/2007 | Larson et al. |
| 2008/0132766 A1 | 6/2008 | Dant et al. |
| 2008/0234550 A1 | 9/2008 | Hawkes et al. |
| 2009/0204067 A1 | 8/2009 | Abu-Halawa |
| 2009/0265941 A1 | 10/2009 | Kurrus |
| 2009/0299148 A1 | 12/2009 | White et al. |
| 2010/0210916 A1 | 8/2010 | Hu et al. |
| 2010/0234689 A1 | 9/2010 | Wagner et al. |
| 2010/0261970 A1 | 10/2010 | Shelton, IV et al. |

FOREIGN PATENT DOCUMENTS

| | | |
|---|---|---|
| DE | 102009014527 | 9/2010 |
| EP | 0177177 | 4/1986 |
| EP | 2179669 | 4/2010 |
| EP | 2 228 014 | 9/2010 |
| EP | 2 228 024 | 9/2010 |

(56) References Cited

FOREIGN PATENT DOCUMENTS

| | | |
|---|---|---|
| EP | 2 238 931 A1 | 10/2010 |
| EP | 2 417 922 | 2/2012 |
| WO | WO95/00197 | 1/1995 |
| WO | WO95/15715 | 6/1995 |
| WO | WO 01/08563 A2 | 2/2001 |
| WO | WO03/034908 | 5/2003 |
| WO | WO2005/089655 | 9/2005 |
| WO | WO 2010/136805 | 12/2010 |
| WO | WO 2011/079374 | 7/2011 |

OTHER PUBLICATIONS

EP Search Report 11 25 0163 dated Jun. 7, 2011.
EP Search Report EP 11 18 9987 dated Feb. 15, 2012.
EP Search Report 11 25 0163 dated Jul. 6, 2011.
EP Search Report EP 12160423.5 dated Jun. 25, 2012.

* cited by examiner

EXPANDABLE THORACIC ACCESS PORT

This application claims priority from provisional application Ser. No. 61/304,111, filed Feb. 12, 2010, the entire contents of which are incorporated herein by reference.

BACKGROUND

1. Technical Field

The present disclosure relates generally to devices and techniques for performing surgical procedures. More particularly, the present disclosure relates to an access device for minimally invasive surgery.

2. Background of the Related Art

In an effort to reduce trauma and recovery time, many surgical procedures are performed through small openings in the skin, such as an incision or a natural body orifice. For example, these procedures include laparoscopic procedures, which are generally performed within the confines of a patient's abdomen, and thoracic procedures, which are generally performed within a patient's chest cavity.

Specific surgical instruments have been developed for use during such minimally invasive surgical procedures. These surgical instruments typically include an elongated shaft with operative structure positioned at a distal end thereof, such as graspers, clip appliers, specimen retrieval bags, etc.

During minimally invasive procedures, the clinician creates an opening in the patient's body wall, oftentimes by using an obturator or trocar, and thereafter positions an access assembly within the opening. The access assembly includes a passageway extending therethrough to receive one or more of the above-mentioned surgical instruments for positioning within the internal work site, e.g. the body cavity.

During minimally invasive thoracic procedures, an access assembly is generally inserted into a space located between the patient's adjacent ribs that is known as the intercostal space, and then surgical instruments can be inserted into the internal work site through the passageway in the access assembly.

In the interests of facilitating visualization, the introduction of certain surgical instruments, and/or the removal of tissue specimens during minimally invasive thoracic procedures, it may be desirable to spread tissue adjacent the ribs defining the intercostal space. Additionally, during these procedures, firm, reliable placement of the access assembly is desirable to allow the access assembly to withstand forces that are applied during manipulation of the instrument(s) inserted therethrough. However, reducing patient trauma during the procedure, discomfort during recovery, and the overall recovery time remain issues of importance. Thus, there exists a need for thoracic access ports which minimize post operative patient pain while enabling atraumatic retraction of tissue and which do not restrict access to the body cavity, as well as facilitates removal of tissue specimens from the body cavity.

SUMMARY

In accordance with the present disclosure, a surgical access assembly, or access port, for positioning within an opening in tissue is provided. The surgical access assembly in one aspect includes first and second wings disposed in opposed relation relative to one another. Each wing includes a body portion, a distal portion, a first portion and a second portion. A first and second side wall section hingedly connects the body portions of the first and second wings to one another. The side wall sections are movable between a first position and a second position wherein each of the side wall sections is angled with respect to the first and second wings. The first and second wings are moveable between an approximated position and a spaced apart position. In the approximated position, the side wall sections are in the first position. In the spaced apart position, the first and second wings are spaced apart from one another defining an opening therethrough and the side wall sections are in the second angled position.

In one embodiment, the access assembly includes a tab that is coupled to each of the body portions of the first and second wings to facilitate grasping and moving the tabs to move the wings between the approximated and spaced apart positions.

In another embodiment, the body portions of the wings are formed from a rigid or a semi-rigid material. The distal portions of the wings may be formed from a rigid or a semi-rigid material. Further, the distal portions may define a curved horizontal cross-sectional configuration.

In some embodiments, the wings are biased toward the approximated position. Alternatively, the wings may be biased toward the spaced apart position. Further, the access assembly may include a locking mechanism configured to lock the first and second wings in the approximated and/or the spaced apart position.

In some embodiments, the distal portions of the first and second wings each define a saddle on an outer surface thereof, each saddle configured to seat a rib of the patient therein. Cushioning may also be provided on an outer surface of the distal portions, e.g. lining the saddles, to provide protection to surrounding tissue.

In some embodiments, the body portions are connected at each end by a pair of side wall sections that may be engaged to one another by a living hinge or a flexible material. The side wall sections may be connected to the body portions by a living hinge or a flexible material.

In some embodiments, the body portions, the distal portions, and the side wall sections are integrally formed as a single piece. The access assembly may have a reduced thickness and/or increased flexibility i.e., a living hinge, at the interconnections between the side wall sections and between the side wall sections and the wings to allow for hinged movement between the approximated position and the spaced apart position.

In another aspect, the present disclosure provides a surgical access assembly for positioning within an opening in tissue comprising first and second members having inner and outer walls and movably connected to one another. The first and second members are movable from a first position wherein the inner walls are closer to one another and a second position wherein the inner walls are further apart. A collapsible member connects a first side portion of the first and second members and is movable from a collapsed position to an expanded position. The access assembly may include a second collapsible member connected to a second side portion of the first and second members. In some embodiments, the first and second collapsible members include a hinged section. Preferably, the first and second members are composed of a more rigid material than the collapsible member.

A method of accessing an internal cavity of a patient is also provided in accordance with another aspect of the present disclosure. The method includes forming an opening in a patient's tissue and providing an access assembly including first and second wings and at least one side wall section hingedly connecting the first and second wings to one another at a first portion and at least one side wall section hingedly connecting the first and second wings to one another at a second portion. The first and second wings are moveable between an approximated position wherein the first and second wings are in a closer spatial relation relative to one another corresponding to the first position of the side wall sections and spaced apart position wherein the first and second wings are spaced apart from one another corresponding to the second position of the side wall sections.

The method further includes the steps of inserting the access assembly through the opening in the approximated position such that the access assembly is positioned within an intercostal space defined between adjacent ribs of the patient and moving the first and second wings of the access assembly from the approximated to the spaced apart position to expand the side wall sections to create a passageway for insertion of surgical instrumentation therethrough.

In some embodiments, each of the side wall sections is hingable with respect to the other side wall sections between a first position wherein each of the side wall sections is substantially parallel with the first and second wings and a second position wherein each of the side wall sections is substantially perpendicular with the first and second wings.

In some embodiments, the movement of the access assembly to the spaced apart position locks the access assembly in the spaced apart position.

Surgical instruments can be inserted through the access assembly in the spaced apart position. The access assembly may be moved from the spaced apart position back to the approximated position for removal of the access assembly from the opening in tissue.

BRIEF DESCRIPTION OF THE DRAWINGS

Various embodiments of the subject access port are described herein with reference to the drawings wherein.

DETAILED DESCRIPTION

Figure 1:
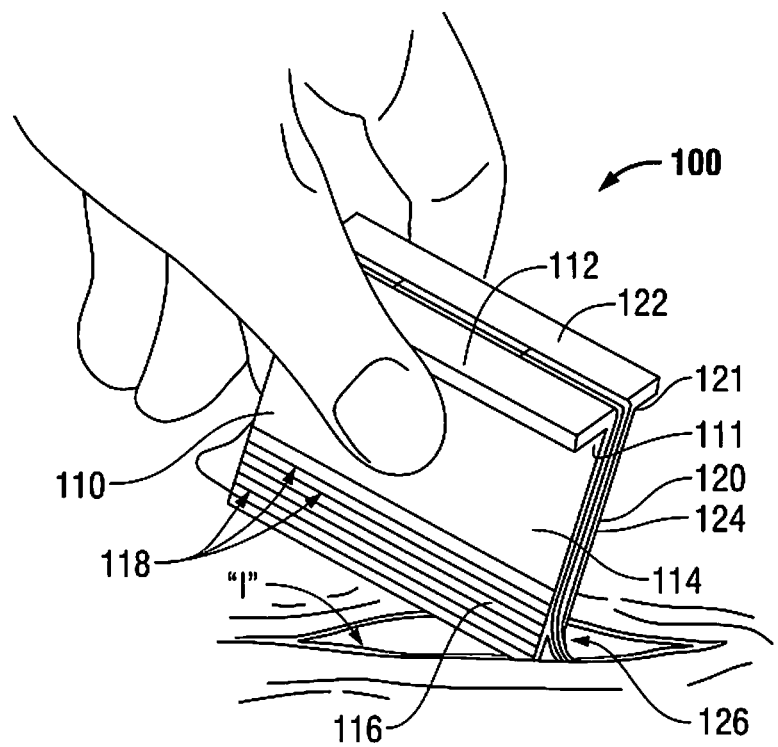
FIG. 1 is a front, perspective view of an access port according to the present disclosure shown being inserted into an incision in the body.

Various embodiments of the presently disclosed access port, or access assembly, and methods of using the same, will now be described in detail with reference to the drawings wherein like references numerals identify similar or identical elements. In the drawings, and in the following description, the term "proximal" should be understood as referring to the end of the access port, or component thereof, that is closer to the clinician during proper use, while the term "distal" should be understood as referring to the end that is farther from the clinician, as is traditional and conventional in the art. Additionally, use of the term "tissue" hereinbelow should be understood to encompass both the patient's ribs, and any surrounding tissues. The term "minimally invasive procedure" is intended to include surgical procedures through small openings/incisions performed within a confined space such as the thoracic cavity.

Referring now to FIGS. 1-4, the presently disclosed surgical access port is shown generally identified by the reference character 100. In the embodiment of FIGS. 1-4, the access port 100 is depicted as a thoracic port 100 that is configured and dimensioned for insertion into the intercostal space located between the adjacent ribs "R" (FIGS. 4 and 5) of a patient in order to allow for the insertion and manipulation of one or more surgical instruments within the thoracic cavity. However, it is also envisioned that access port 100 may be configured and dimensioned to provide access to a variety of other internal body cavities and/or tissues during minimally invasive surgical procedures. Further, access port 100 may be formed from any suitable biocompatible material of a strength suitable for the purpose described herein, including, but not being limited to, polymeric materials.

Figure 4:
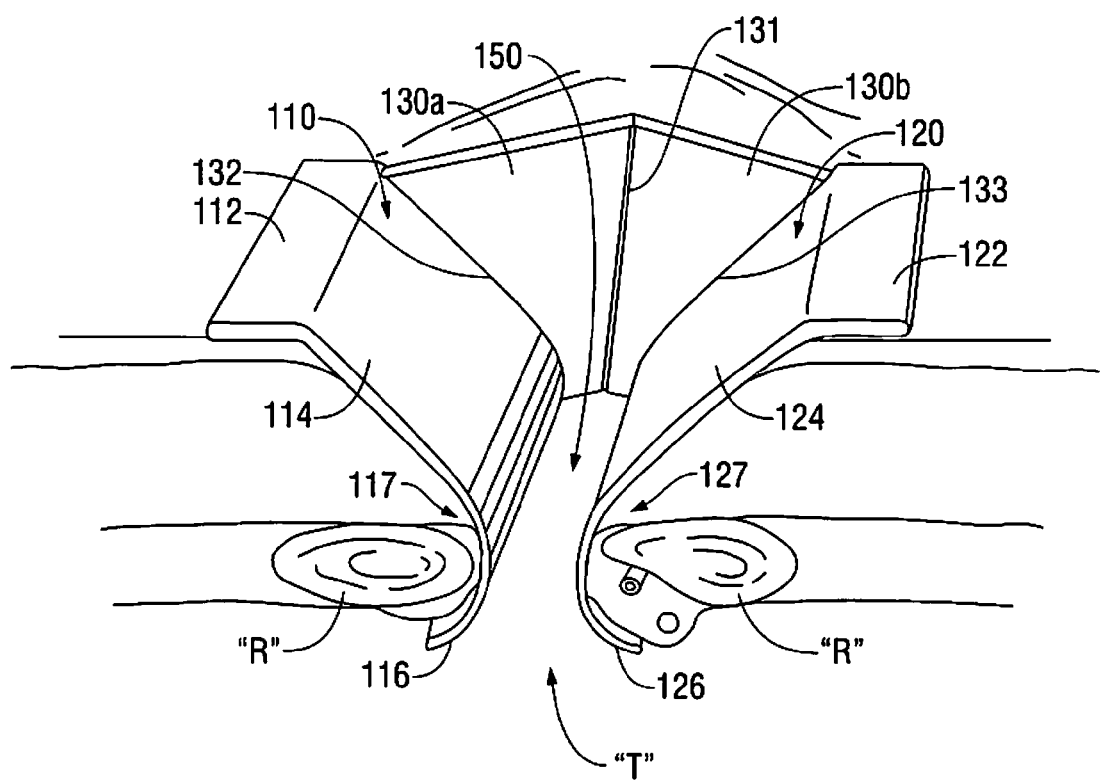
FIG. 4 is a cross-sectional view of the access port of FIG. 1 shown disposed through an incision in tissue in the spaced apart position.
Figure 5:
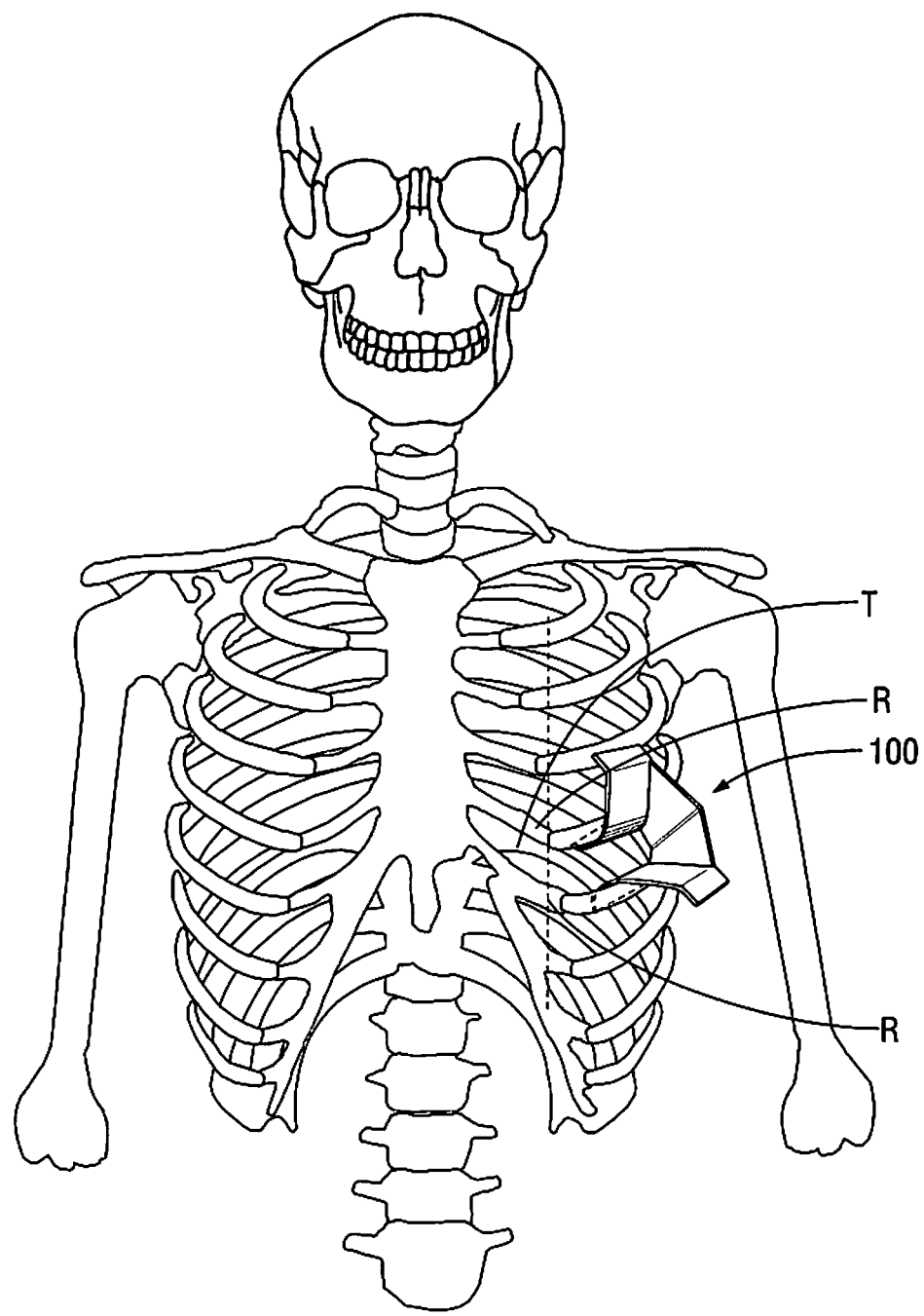
FIG. 5 is a front view illustrating a patient's skeletal structure with the surgical access port of FIG. 1 positioned in the spaced apart position within the intercostal space defined between adjacent ribs.

The access port 100 is configured and dimensioned to extend into a body cavity, e.g., the thoracic cavity "T" (FIG. 4), through the intercostal space (see FIG. 5), and includes first and second opposed wings 110 and 120 interconnected on opposing ends by a pair of expandable side walls 130, 140. First and second tabs 112, 122 extend outwardly from proximal portions 111, 121 of first and second wings 110 and 120, respectively, to facilitate movement of the wings 110, 120 between an approximated position (FIG. 1) and a spaced apart position (FIG. 4).

More specifically, as shown in FIG. 1, first and second opposed wings 110 and 120 each include a proximal portion 111, 121, a body portion 114, 124 and a distal portion 116, 126. Tabs 112, 122 may include one or more enhanced gripping features (not explicitly shown) to facilitate the gripping of tabs 112, 122 (see FIG. 2) during movement between the approximated and spaced apart positions. Tabs 112, 122 may be formed integrally/monolithically with, or may be fixedly attached to the respective body portions 114, 124. Further, tabs 112, 122 may be flexible or deflectable with respect to body portions 114, 124 from a substantially perpendicular configuration (FIG. 1) to an acute configuration or to an obtuse configuration in which the angle formed between tabs 112, 122 and body portions 114, 124, respectively, is greater than 90 degrees.

Body portions 114, 124 are generally thin and flat and are dimensioned for insertion into an incision "I" in the intercostal space. Thus, body portions 114, 124 may have a length similar to, or slightly less, or slightly greater, than the length of the incision "I" through which access port 100 is to be inserted. Different lengths are also contemplated. Further, body portions 114, 124 may be configured according to the length of the incision "I," which may depend on the particular surgical procedure to be performed. Body portions 114, 124 may be formed from a semi-rigid material such that, upon movement of tabs 112, 122 apart from one another, body portions 114, 124 are moved to a spaced apart position substantially along a length thereof. In other words, it is envisioned that body portions 114, 124 be sufficiently rigid such that the proximal ends of body portions 114, 124 are moved apart and not simply bent in response to moving tabs 112, 122 apart from one another. Body portions 114, 124 may also have some degree of flexibility to reduce the likelihood of breaking the access port 100 and to reduce the force exerted on surrounding tissue.

Distal portions 116, 126 of wings 110, 120, respectively, extend distally from body portions 114, 124 and define generally curved configurations. More particularly, each distal portion 116, 126 is curved to define an outwardly facing saddle 117, 127. As will be described in more detail below, distal portions 116, 126 are configured for positioning between adjacent ribs "R" of a patient (FIGS. 4 and 5), such that each adjacent rib "R" is seated within one of the outwardly facing saddles 117, 127. Cushioning (not explicitly shown) may be provided on the outer surface of distal portions 116, 126, i.e., lining the outwardly facing saddles 117, 127, to provide additional protection to tissue and nerves surrounding the adjacent ribs "R."

Distal portions 116, 126 of wings 110, 120 may be formed integrally/monolithically with, or may be fixedly attached to body portions 114, 124. The interfaces between distal portions 116, 126 and body portions 114, 124, respectively, may be somewhat flexible such that, as access port 100 is moved to the spaced apart position, body portions 114, 124 may be deflected with respect to distal portions 116, 126 to create a funnel-shaped passageway 150 (FIG. 4) extending through access port 100. This may be accomplished in some embodiments by a reduced thickness portion and/or an increased flexibility portion between distal portions 116, 126 and body portions 114, 124, respectively. Further, distal portions 116, 126 may be formed from a rigid or semi-rigid material to provide structural integrity to distal portions 116, 126. This structural integrity maintains the curved configurations of distal portions 116, 126 during movement of the tabs 112, 122 and body portions 114, 124 between the approximated and spaced apart positions. Additionally, use of a rigid material would allow distal portions 116, 126 to better separate tissue adjacent ribs "R," and/or in some embodiments ribs "R," providing greater access to the thoracic cavity. Reinforcements (not shown), for example, may extend substantially along a length or portion thereof, of distal portions 116, 126 and/or may be disposed therein to limit the flexibility of distal portions 116, 126 to maintain the curved configurations of saddle portions 117, 127. Alternatively, where wings 110, 120 are formed from sufficiently rigid material, distal portions 116, 126 may include a series of channels, slits, or grooves 118 extending therealong to help define the curved configuration of the distal portions 116, 126.

Figure 3A:
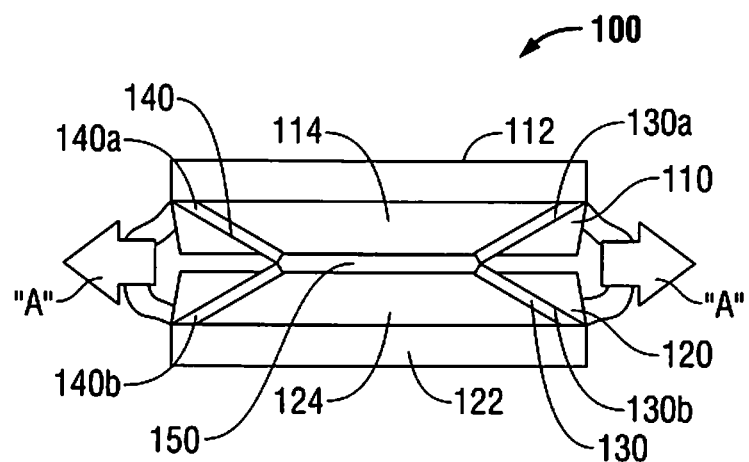
FIG. 3A is a top view of the access port of FIG. 1 showing the access port being expanded from the approximated position towards a spaced apart position.
Figure 3B:
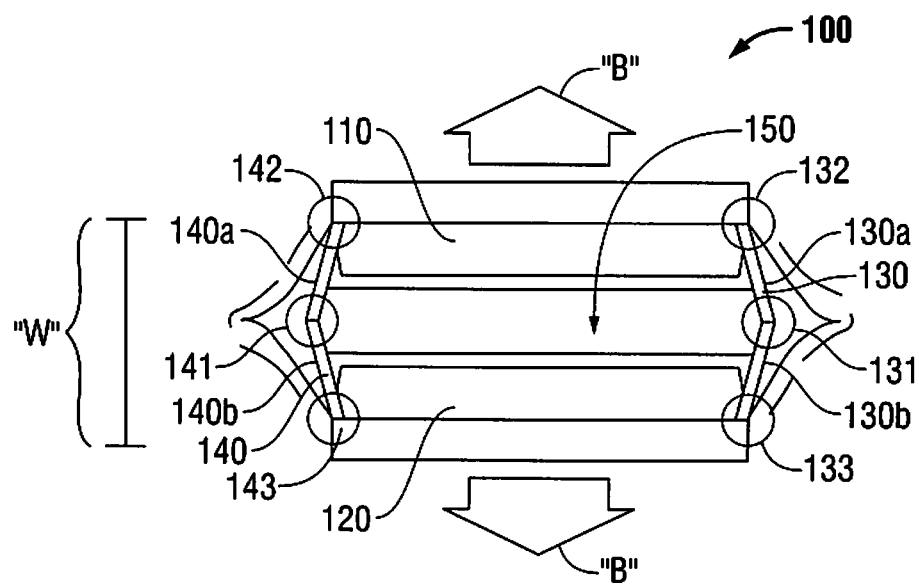
FIG. 3B is a top view of the access port of FIG. 1 showing the access port being further expanded towards the spaced apart (expanded) position.

As best shown in FIGS. 3A-3B, and as mentioned above, wings 110, 120 are interconnected by a pair of expandable/collapsible side walls 130, 140, respectively. Each expandable side wall 130, 140 includes first and second wall sections 130a, 130b and 140a, 140b, respectively, hingedly connected to one another via hinges 131, 141, respectively, at one end thereof. Wall sections 130a, 140a are hingedly attached at the other ends to the side portions of wing 110 via hinges 132, 142, respectively, while wall sections 130b, 140b are hingedly attached at the other ends to the side portion of wing 120 via hinges 133, 143, respectively. As can be appreciated, an expandable access port 100, having a passageway 150 extending therethrough is defined by the above-described configuration of wings 110, 120 and expandable side walls 130, 140.

More particularly, expandable side walls 130, 140 are generally thin, flat members that may be formed from a rigid or semi-rigid material. The side wall sections 130a, 130b of expandable side wall 130 and the side wall sections 140a, 140b of expandable side wall 140 may be connected via a living hinge 131, 141, respectively, e.g., a reduced thickness or increased flexible material, such that wall sections 130a, 130b and 140a, 140b may be angled with respect to each other about their interconnected ends between sections 130a, 140a and 130b, 140b, respectively. Alternatively, any other hinge-like mechanism may be used to join side wall sections 130a and 130b and/or side wall sections 140a and 140b. Side wall sections 130a, 130b, 140a, 140b may be similarly attached to the respective ends of wings 110, 120 via a living hinge (132, 133, 142, 143) or other hinge mechanism, to permit wall sections 130, 140 to be moveable, or angleable, with respect to wings 110, 120. Further, side walls 130, 140 are preferably generally quadrilateral in shape, decreasing in width proximally to distally to complete the funnel-shaped configuration of access port 100 when in the spaced apart position. Other shapes are also contemplated. More particularly, as body portions 114, 124 are moved apart from one another, body portions 114, 124 are translated and angled outwardly with respect to distal portions 116, 126 such that passageway 150 defines a greater width toward the proximal end of access port 100 and a smaller width towards a distal end of access port 100. Thus, the side walls 130, 140 are shaped to accommodate the funnel-shaped configuration of the access port 100.

It is envisioned that wall sections 130a, 130b be moveable about living hinge 131 with respect to one another between a first position, wherein wall sections 130a and 130b are mating, or flush with one another, i.e., where the angle between wall sections 130a and 130b approaches about 0 degrees (see FIG. 2), and a second position wherein wall sections 130a and 130b are abutting each other, i.e. where the angle between wall sections 130a and 130b approaches (or exceeds) about 180 degrees (see FIG. 3B). Other angles are also contemplated. Similarly, wall sections 140a and 140b may also be configured to be moveable about living hinge 141 between a first position where the angle between wall sections 140a and 140b approaches about 0 degrees (FIG. 2), and a second position where the angle between wall sections 130a and 130b approaches (or exceeds) about 180 degrees (FIG. 3B). Other angles are also contemplated.

Moreover, it is envisioned that wall sections 130a and 140a also be moveable about living hinges 132 and 142 with respect to wing 110 between a first position wherein wall sections 130a and 140a are substantially parallel with wing 110 such that the angle formed between either (or both) of the wall sections 130a and 140a and wing 110 approaches about 0 degrees (see FIG. 2) and a second position wherein wall sections 130a and 140a are substantially perpendicular (or further angled from wing 110) such that the angle formed between either (or both) of the wall sections 130a and 140a and wing 110 approaches (or exceeds) about 90 degrees (see FIG. 3B). Other angles are also contemplated. Wall sections 130b, 140b and wing 120 may be similarly moveable about living hinges 133 and 143 with respect to one another as wall sections 130a, 140a and wing 110, described above and thus it is envisioned they form similar angles to wing 120 as wall sections 130a, 140a form with wing 110.

Figure 2:
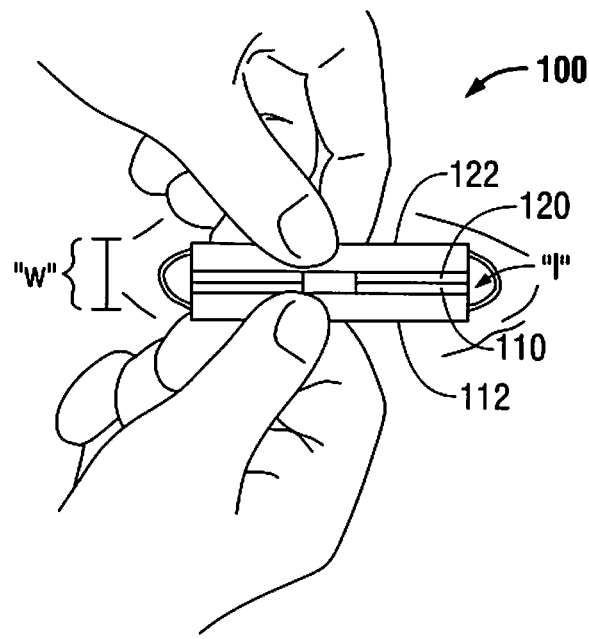
FIG. 2 is a top view of the access port of FIG. 1 showing a user grasping tabs of the access port to move the access port from an approximated position.

As can be appreciated, due to the various hinge-like connections of wings 110, 120 and side walls 130, 140, access port 100 may be expanded from an approximated position (FIGS. 1 and 2), wherein the inner walls of body portions 114, 124 are closer to one another and the passageway 150 therethrough is reduced, and preferably substantially closed off, to a spaced apart (spread) position (FIG. 4), wherein the inner walls of body portions 114, 124 are moved further apart and the passageway 150 is opened to a configuration to allow insertion of surgical instrumentation therethrough. In other words, in the approximated position, the position of side wall sections 130a, 130b and side wall sections 140a, 140b with respect to each other is about 0 degrees (FIG. 2), and wherein the angle between the side wall sections 130a, 130b and 140a, 140b and the respective wings 110, 120 is about 0 degrees (FIG. 2). Accordingly, in the approximated position of this embodiment, as best shown in FIGS. 1 and 2, wing 110, side wall sections 130a and 140a, side wall sections 130b and 140b, respectively, and wing 120 are substantially parallel.

Thus, the access port 100 is in an approximated position, defining a minimum width "w". It is also contemplated that alternatively in the approximated position, the side walls can be at an angle to rather than substantially parallel to the wings.

As will be described in more detail below, moving tabs 112, 122 apart from one another moves wings 110, 120 from the approximated position to the spaced apart (expanded) position, which simultaneously angles side wall sections 130a, 130b, 140a, 140b with respect to each other about living hinges 131 and 141 and with respect to wings 110, 120 about living hinges 132, 133, 142, and 143, respectively, such that the access port 100 is moved to the spaced apart position defining the passageway 150 therebetween.

With reference to FIG. 3B, in the spaced apart position (or positions) of access port 100, the angle between the respective wall sections 130a, 130b and 140a, 140b approaches (or exceeds) about 180 degrees, and the angle between the wall sections 130a, 130b and 140a, 140b and the respective wings 110, 120 approaches (or exceeds) about 90 degrees. As noted above, other angles are also contemplated. Accordingly, in this spaced apart position, as best shown in the embodiment of FIG. 3B, wings 110, 120 and expandable side walls 130, 140 form a passageway 150 therethrough having a substantially rectangular top cross-sectional profile (where the angles between the side wall sections 130a-b, 140a-b and between the side walls 130, 140 and the wings 110, 120 are about 180 degrees and about 90 degrees, respectively). Other profiles are also contemplated. As mentioned above, the side cross-sectional profile of the wings 110, 120 and side walls 130, 140 preferably define a generally funnel, or conical shape when in the open, or spaced apart position. Further, this spaced apart position, wherein passageway 150 extends through access port 100, defines a maximum width "W" of access port 100, greater than width "w" of FIG. 2.

Although one embodiment of access port 100 is described above and shown in FIGS. 1-4, it is envisioned that the specific configuration and dimensions of the access port 100 may be varied in alternative embodiments of the present disclosure based on factors such as the anatomy of the patient to be treated, and the surgical instruments to be used in conjunction therewith. As such, it is further envisioned that the wings 110 and 120 and/or side walls 130, 140 may include arcuate, or other non-linear portions to, for example, enlarge the passageway 150 defined therebetween. Further, it is envisioned that the access port 100 can be constructed as a single piece, and may be disposable after a single use.

With reference now to FIGS. 1-4, the use and operation of the access port 100 will be discussed during the course of a minimally invasive thoracic procedure by way of example, it being understood that the access port 100 can be used in other minimally invasive surgical procedures and in other parts of the body. As will be appreciated in view of the following, access port 100 is easily insertable, deployable, and removable from a patient's body.

Initially, an opening, or incision "I," is made in the patient's outer tissue wall of the thoracic body cavity by conventional means. The incision "I" is made between adjacent ribs "R," extending along the intercostal space. In other words, a relatively narrow, elongated incision "I" is made between adjacent ribs "R."

For insertion into the incision "I," access port 100 is in the approximated position, wherein, as mentioned above, wings 110, 120 and side walls 130, 140 are substantially parallel with one another to define a minimum width "w". When in the approximated position, as can be appreciated, the passageway 150 extending though access port 100 is narrowed and can be substantially closed off. Further, it is envisioned that the minimum width "w" be sufficiently small to allow access port 100 to be inserted at least partially through incision "I" when in the approximated position. Accordingly, access port 100 may be configured to define different minimum widths, depending on the anatomy of the patient and/or on the specific procedure to be performed.

As shown in FIG. 1, access port 100 is inserted partially through the incision "I" and is positioned lengthwise through the elongated incision "I." Access port 100 is inserted through the incision "I" until distal portions 116, 126 of wings 110, 120 are disposed adjacent ribs "R" and, more specifically, such that each rib "R" is generally aligned with a corresponding saddle 117, 127 of the distal portions 116, 126 of wings 110, 120, respectively.

Referring now to FIG. 2, once access port 100 is positioned as described above, the user grasps and pulls tabs 112, 122 in opposite directions, thereby spreading wings 110 and 120 apart from one another, as shown by arrows "B" FIG. 3B. As wings 110, 120 are spread apart from one another, body portions 114, 124 are spread apart from one another, side wall sections 130a, 140a and side wall sections 130b, 140b are moved outwardly, as indicated by arrows "A" (FIG. 3A), to angle side walls 130, 140 with respect to body portions 114, 124, thereby expanding the passageway 150 extending through access port 100. FIG. 3A shows an intermediate position of access port 100 wherein the passageway 150 has been expanded partially and wherein the angles between the side wall sections 130a-b, 140a-b are greater than about 0 degrees but less than about 180 degrees and wherein the angles between the side walls 130, 140 and the wings 110, 120 are greater than about 0 degrees but less than about 90 degrees. Such intermediate positioning enables different size passageways to accommodate different anatomy.

As can be appreciated, spreading wings 110, 120 apart from one another causes distal portions 116, 126 of wings 110, 120, respectively, to spread apart, although body portions 114, 124 may be configured to deflect further with respect to distal portions 116, 126 such that the passageway 150 is generally funnel-shaped. The spreading of distal portions 116, 126 engages each saddle portion 117, 127 with tissue adjacent a respective rib "R," thereby urging the tissue adjacent the ribs "R" apart. Cushioning (not explicitly shown) may line the saddle portions 117, 127 to help prevent tissue, and more particularly, nerve damage. Thus, access port 100 may be configured to expand to about the width of the intercostal space. In other words, in this embodiment, distal portions 116, 126 would engage tissue adjacent ribs "R" within saddle portion 117, 127, but would not urge ribs "R" apart. Rather, access port 100 would simply define an opening through the at-rest intercostal space, spreading tissue adjacent the incision and ribs. That is, access port 100 may be configured to retract soft tissue surrounding ribs "R" to expand the access area while not increasing the distance between adjacent ribs "R." In alternate embodiments, portions 116 and 126 can be configured to urge adjacent ribs "R" apart from one another, further expanding the intercostal space.

As shown in FIG. 3B, as tabs 112, 122 are pulled further apart from one another, to a further extended, or spaced apart position, passageway 150 is expanded further, the extent of expansion depending on the tissue, and with the maximum expansion shown as a maximum width "W." This maximum width "W" is achieved when side wall sections 130a-b, 140a-b are fully open and angled about 180 degrees with respect to each other and, thus, when the side walls 130, 140 are substantially perpendicular with respect to the wings 110, 120. Side wall sections 130a-b and 140a-b may be configured to angle past about 180 degrees with respect to each other, thereby allowing side walls 130, 140 to angle greater than about 90 degrees with respect to wings 110, 120, respectively. Further, a one-way locking mechanism (not explicitly shown) may be provided to prevent access port 100 from collapsing back to the approximated position. The locking mechanism would prevent side wall sections 130*a-b* and 140*a-b* from angling inwardly toward the approximated position once a pre-determined angle has been achieved. For example, the locking mechanism may prevent approximation of the wings 110, 120 by preventing the wall sections 130*a-b* and 140*a-b* from being moved with respect to each other to less than about 180 degrees, once the about 180 degree threshold has been met or surpassed. Thus, in this embodiment, once tabs 112, 122 are expanded such that side wall portions 130*a-b* and 140*a-b* are moved to open or spread position and side walls 130 and 140 are moved outwardly to (or past) a substantially perpendicular position with respect to wings 110 and 120, the user may release the tabs 112, 122 and access port 100 remains locked in the open, or spaced apart position. As will be described in more detail hereinbelow, the access port 100 may be collapsed back to the approximated position by squeezing tabs 112, 122 toward each other, by manually collapsing side wall sections 130*a-b*, 140*a-b*, and/or by use of a release mechanism (not shown) configured to release (unlock) access port 100 from the spaced apart position.

It is envisioned that the maximum width "W" of access port 100 may be greater than a width defined between adjacent ribs "R" such that, when access port 100 is expanded to the spaced apart position, adjacent ribs "R" are urged apart from one another. In such an embodiment, the locking mechanism (not shown) may be used to prevent the adjacent ribs "R" from moving back toward each other to their at-rest position. Alternatively, as mentioned above, preferably the width "W" may be equal to or less than the intercostal spacing such that the ribs "R" are not disturbed during insertion, use, and/or removal of access port 100. In either embodiment, the access port 100 is configured and dimensioned to provide good visibility through the incision and into the surgical site when in the spaced apart position.

Referring now to FIG. 4, the access port 100 is shown inserted into the incision "I" between adjacent ribs "R." Tabs 112, 122 are deflected relative to wings 110, 120, respectively, such that tabs 112, 122 extend from the incision "I" along an exterior surface of tissue to protect tissue surrounding the incision "I." Body portions 114, 124 of wings 110, 120, extend through the incision "I," providing an expanded, funnel-shaped passageway 150 therethrough and protecting the inner surfaces of the incision "I." Distal portions 116, 126 of wings 110, 120 conform at least partially to ribs "R" and retain ribs "R" in the spaced apart position, while protecting surrounding tissue and nerves. Further, a lubricious coating may be provided on the inner surface of wings 110, 120 to facilitate insertion and/or removal of surgical instrumentation and tissue from inside the thoracic cavity.

Once the access port 100 is disposed in the spaced apart position, as shown in FIG. 4, surgical instrumentation (not shown) may be inserted through the passageway 150 extending through access port 100 to perform surgical, diagnostic, or other procedures within the thoracic cavity. As mentioned above, access port 100 not only provides an expanded passageway 150, thereby allowing greater visibility and access to the thoracic cavity, but also protects surrounding tissue from potential damage during insertion, manipulation, and removal of surgical instrumentation and/or tissue specimens through the access port 100.

Following completion of the surgical purpose, the instrumentation (not shown) can be removed from access port 100 and access port 100 can be collapsed to the approximated position for removal from the intercostal space. To collapse the access port 100, the user may squeeze tabs 112, 122 toward each other such that side walls 130, 140 are collapsed inwardly and wings 110 and 120 are returned to the approximated position. In embodiments where a locking mechanism is used, or where the side walls 130, 140 are angled greater than 180 degrees with respect to each other to a "locked" position, it may be necessary to manually collapse side wall sections 130*a*, 130*b* and/or side wall sections 140*a*, 140*b* of expandable side walls 130, 140, respectively, prior to squeezing tabs 112, 122. Alternatively, a release mechanism (not shown) may be included to release access port 100 from the spaced apart, locked position. Once collapsed back to the approximated position, the access port 100, having a minimized width, (such as in FIG. 2) may easily be removed from the incision "I." Finally, the incision "I" may be closed off via conventional means.

Persons skilled in the art will understand that the devices and methods specifically described herein and illustrated in the accompanying figures are non-limiting exemplary embodiments, and that the description, disclosure, and figures should be construed merely exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Accordingly, the subject matter of the present disclosure is not to be limited by what has been particularly shown and described.

What is claimed is:

1. A surgical access assembly for positioning within an opening in tissue, the surgical access assembly comprising:

first and second wings disposed in opposed relation relative to one another, each wing including a body portion, a distal portion and first and second portions;

a first side wall section hingedly connecting the body portions of the first and second wings to one another at the first portion of each of the body portions and a second side wall section hingedly connecting the body portions of the first and second wings to one another at the second portion of each of the body portions, the side wall sections being movable between a first position, wherein the side wall sections are disposed within an outer dimension defined by the first and second wings, and a second position wherein each of the side wall sections are angled outwardly to extend from the outer dimension defined by the first and second wings; and wherein, the first and second wings are moveable between an approximated position corresponding to the first position of the side wall sections and a spaced apart position corresponding to the second position of the side wall sections.

2. The access assembly according to claim 1, wherein the side wall sections are substantially parallel with the first and second wings in the first position and the access assembly further comprises a tab coupled to each of the wings of the first and second wings such that grasping and moving the tabs moves the wings between the approximated and spaced apart positions.

3. The access assembly according to claim 1, wherein the body portions are formed from one of a rigid and a semi-rigid material.

4. The access assembly according to claim 1, wherein the distal portions of the first and second wings define a curved horizontal cross-sectional configuration.

5. The access assembly according to claim 1, wherein the wings are biased in one of the approximated and spaced apart positions.

6. The access assembly according to claim 1, wherein each of the distal portions of the first and second wings define a saddle on an outer surface thereof, each saddle configured to seat a rib of a patient therein.

7. The access assembly according to claim 1, further comprising cushioning disposed on an outer surface of the distal portions to provide protection to surrounding tissue.

8. The access assembly according to claim 1, wherein a pair of hingedly engaged side wall sections connect the first ends of the body portions and wherein a pair of hingedly engaged side wall sections connect the second ends of the body portions.

9. The access assembly according to claim 8, wherein the side wall sections of each pair of side wall sections are engaged to one another by a hinge.

10. The access assembly according to claim 1, wherein the body portion, the distal portions, and the side wall sections are integrally formed as a single piece, interconnected by a plurality of living hinges.

11. The access assembly according to claim 1, wherein in the spaced apart position of the wings a funnel shaped passageway is formed.

12. A surgical access assembly for positioning within an opening in tissue, comprising:
  first and second members having inner and outer walls and movably connected to one another, the first and second members being movable from a first position wherein the inner walls are closer to one another to a second position wherein the inner walls are further apart, the first and second members further having proximal and distal portions and first and second side portions defined between the proximal and distal portions; and
  a collapsible member connected to the first side portion of the first and second members to connect the first and second members, the collapsible member movable from a collapsed position, wherein the collapsible member is flexed inwardly towards the first and second members, to an expanded position, wherein the collapsible member is angled outwardly to extend from the first and second members.

13. The access assembly according to claim 12, wherein the collapsible member comprises a hinged section.

14. The access assembly according to claim 12, further comprising a second collapsible member connected to the second side portion of the first and second members, wherein the second collapsible member comprises a hinged section.

15. The access assembly according to claim 12, wherein the first and second members are composed of a more rigid material than the collapsible member.

16. The access assembly according to claim 12, further comprising a second collapsible member connected to the second side portion of the first and second members and movable to an expanded position, the collapsible members locking in the expanded position.

* * * * *